US010687829B2

(12) United States Patent
Singh et al.

(10) Patent No.: US 10,687,829 B2
(45) Date of Patent: Jun. 23, 2020

(54) SYSTEMS AND METHODS FOR PLACEMENT OF SURGICAL INSTRUMENTATION

(71) Applicant: MIRUS LLC, Atlanta, GA (US)

(72) Inventors: Angad Singh, Marietta, GA (US); Philip Matthew Fitzsimons, Lilburn, GA (US); Yasser Boumenir, Douglasville, GA (US)

(73) Assignee: MiRus LLC, Marietta, GA (US)

( * ) Notice: Subject to any disclaimer, the term of this patent is extended or adjusted under 35 U.S.C. 154(b) by 197 days.

(21) Appl. No.: 15/558,352

(22) PCT Filed: Mar. 24, 2016

(86) PCT No.: PCT/US2016/024022
§ 371 (c)(1),
(2) Date: Sep. 14, 2017

(87) PCT Pub. No.: WO2016/154442
PCT Pub. Date: Sep. 29, 2016

(65) Prior Publication Data
US 2018/0085135 A1 Mar. 29, 2018

Related U.S. Application Data

(60) Provisional application No. 62/137,649, filed on Mar. 24, 2015.

(51) Int. Cl.
*A61B 17/56* (2006.01)
*A61B 17/60* (2006.01)
(Continued)

(52) U.S. Cl.
CPC .......... *A61B 17/1707* (2013.01); *A61B 34/20* (2016.02); *A61B 90/06* (2016.02);
(Continued)

(58) Field of Classification Search
CPC combination set(s) only.
See application file for complete search history.

(56) References Cited

U.S. PATENT DOCUMENTS

| 5,928,231 A | 7/1999 | Klein et al. |
| 6,587,750 B2 | 7/2003 | Gerbi et al. |
| (Continued) | | |

FOREIGN PATENT DOCUMENTS

WO 2014063181 A1 5/2014

OTHER PUBLICATIONS

Extended European Search Report dated Oct. 26, 2018 in corresponding European Application No. 16769698.8 (9 pages).
(Continued)

*Primary Examiner* — Sameh R Boles
(74) *Attorney, Agent, or Firm* — Meunier Carlin & Curfman LLC (57) ABSTRACT

A system and method is provided for estimating orientation and position of surgical instrumentation or tools relative to a patient's bone structure. The system and/or method may include registering an axis and/or plane associated with a patient's bone. The system and/or method may further include receiving, from magnetic and orientation sensors, information indicative of orientation and position of the surgical instrument or tool relative to the registered axis and/or plane.

19 Claims, 5 Drawing Sheets

(51) Int. Cl.
  *A61F 2/00* (2006.01)
  *A61B 17/17* (2006.01)
  *A61F 2/32* (2006.01)
  *A61F 2/46* (2006.01)
  *A61B 34/20* (2016.01)
  *A61B 90/00* (2016.01)

(52) U.S. Cl.
  CPC .................. *A61F 2/32* (2013.01); *A61F 2/46* (2013.01); *A61B 2034/2048* (2016.02); *A61B 2034/2051* (2016.02); *A61B 2034/2059* (2016.02); *A61B 2090/067* (2016.02)

(56) References Cited

U.S. PATENT DOCUMENTS

| | | |
|---|---|---|
| 8,718,820 B2 | 5/2014 | Amiot et al. |
| 9,339,226 B2 | 5/2016 | van der Walt et al. |
| 2004/0153066 A1 | 8/2004 | Coon et al. |
| 2004/0243148 A1 | 12/2004 | Wasielewski |
| 2005/0251026 A1 | 11/2005 | Stone |
| 2008/0051910 A1 | 2/2008 | Kammerzell et al. |
| 2011/0275957 A1 | 11/2011 | Bhandari |
| 2012/0022406 A1 | 1/2012 | Hladio et al. |
| 2012/0157887 A1 | 6/2012 | Fanson et al. |
| 2013/0218007 A1 | 8/2013 | Petteys et al. |
| 2013/0231672 A1 | 9/2013 | Paradis et al. |
| 2014/0276864 A1 | 9/2014 | Aghazadeh |

OTHER PUBLICATIONS

International Search Report and Written Opinion dated Jun. 13, 2016 in corresponding PCT application No. PCT/US2016/024022.

SYSTEMS AND METHODS FOR PLACEMENT OF SURGICAL INSTRUMENTATION

CROSS-REFERENCE TO RELATED APPLICATIONS

This application is a national stage application filed under 35 U.S.C. § 371 of PCT/US2016/024022 filed Mar. 24, 2016, which claims the benefit of U.S. Provisional Patent Application No. 62/137,649, filed on Mar. 24, 2015, entitled "SYSTEMS AND METHODS FOR PLACEMENT OF SURGICAL INSTRUMENTATION," the disclosure of which is expressly incorporated herein by reference in its entirety.

TECHNICAL FIELD

The present disclosure relates generally to orthopedic surgery and, more particularly, to a system and method for intra-operatively measuring placement parameters for surgical instrumentation and tools used during orthopedic arthroplastic procedures.

BACKGROUND

Orthopedic procedures involve resurfacing, replacement, or reconstruction of joints using multi-component prosthesis with articulating surfaces. In such procedures proper placement of the prosthetic component is critical for longevity of the implant, positive clinical outcomes, and patient satisfaction. Often this requires surgical instrumentation for proper cutting or re-shaping of the bone to accommodate the prosthetic component. For example, in knee replacement surgery, cutting guides or blocks that are positioned using mechanical guides are utilized to make cuts on the patient's bone. The orientation and position of such cuts with respect to anatomic axes and/or landmarks is critical to ensure proper placement of the prosthetic component. This requires precise placement of the cutting guides or blocks.

Existing methods for placement of the cutting guides or blocks typically require the use of rudimentary mechanical instrumentation that are bulky, cumbersome, and add time to the procedure. There are also prone to errors depending of the subjective assessment and experience level of the surgeon. Some computer/robotically-assisted surgical systems provide a platform for more reliably estimating cut placement parameters. These systems typically require complex and sophisticated tracking equipment, bulky markers/sensors, time-consuming instrument calibration/registration procedures, and highly-specialized software packages that often require technical support personnel to work with doctor in the operating room. Not only do such systems tend to be costly, they also tend to be far too complex to warrant broad adoption among orthopedic surgeons.

To overcome the accuracy and reliability issues associated with manual methods for determining joint placement parameters, while providing a cost-effective and relatively user-friendly approach that is unavailable in computer/robotically-assisted systems, a cost-effective, portable, and user-friendly tool and associated methods for placement of surgical instrumentation would be advantageous. The presently disclosed system and associated methods for intra-operatively measuring surgical instrument placement parameters during orthopedic arthroplastic procedures are directed to overcoming one or more of the problems set forth above and/or other problems in the art.

SUMMARY

According to one aspect, the present disclosure is directed to a method for estimating an orientation and position for placement of a cutting guide on a patient's bone, and includes registering an axis and/or plane associated with the bone. For example, for femoral or tibial resection in total knee arthroplasty (TKA), the method may include rigid fixation of orientation sensors on the patient's bone and receiving from these sensors information indicative of the orientation of the bone's mechanical axis and/or anatomic planes. The orientation of the mechanical axis and/or anatomic planes may be derived using kinematic methods which may include moving the patient's bone, and the rigidly affixed sensors, through a specified series of motions and receiving from the sensor information indicative of rotation axes and/or planes of rotation from which information the mechanical axis and/or anatomic planes may be derived. The orientation for the mechanical axis may also be derived by aligning the sensors to anatomic landmarks using intramedullary or extramedullary rods and/or pins. The method further includes estimating at least one angle of a cutting guide relative to an axis or plane associated with the bone by receiving orientation information from sensors rigidly coupled to the cutting guide.

In accordance with another aspect, the present disclosure is directed to a method for estimating a position for placement of a cutting guide on a patient's bone. The method includes estimating a first position of the cutting guide relative to an anatomic surface of interest, such as the condylar surface, and then tracking the position of a magnetic field generator attached to the cutting guide by receiving information from a magnetic sensors (also known as magnetometers) that measure the relative motion of the cutting guide with respect to anatomic surface of interest. In order to measure the relative motion of the cutting guide with respect to anatomic surface of interest in some implementations, the magnetic field generator may be attached to the cutting guide, and the magnetic sensors may be attached to the anatomic surface of interest. In order to measure the relative motion of the cutting guide with respect to anatomic surface of interest in other implementations, the magnetic field generator may be attached to the anatomic surface of interest, and the magnetic sensors may be attached to the cutting guide. Alternatively or additionally, mechanical methods of estimating and displaying position of a cutting guide may be utilized such as by moving the cutting guide on sliding graduated scale that is mechanically referenced to an anatomic surface of interest.

In accordance with another aspect, the present disclosure is directed to a system for estimating an orientation and position of a cutting guide or other surgical instrument relative to the anatomy of a patient. The system includes orientation and magnetic sensors coupled to a patient's bone. The system may also include an orientation sensor and magnetic field generator, such as a permanent magnet, coupled to the cutting guide. The system also includes a processor, communicatively coupled to the orientation sensors and magnetic sensors. The processor may be configured to register one or more axes or planes associated with a patient's bone. The processor may be further configured to estimate an angle between the cutting guide and at least one of an axis or plane. The processor may be further configured to estimate the position of the cutting guide from an anatomic surface.

In accordance with another aspect, the present disclosure is directed to a system for automated positioning of a cutting guide or surgical instrument relative to the anatomy of a patient. In addition to the components described above, the system includes robotic actuators for automated rotation and translation of the cutting guide to a pre-specified position per the surgeon's operative plan.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Systems and methods consistent with the embodiments disclosed herein are directed to a sensor-based system to measure orientation and position of a cutting guide relative to the patient's anatomy. The system does not rely on expensive tracking or robotic equipment. Systems and methods consistent with the disclosed embodiments also limit the number of hardware components and steps needed to calibrate the system for use, potentially reducing the time and cost burden associated with the procedure. Certain exemplary embodiments can be described as "imageless," meaning that they do not rely on any pre-operative or intra-operative imaging (X-ray, CT or MRI), which can add additional time and cost to the procedure and subject the patent to unnecessary exposure to potentially harmful radiation.

Figure 1:
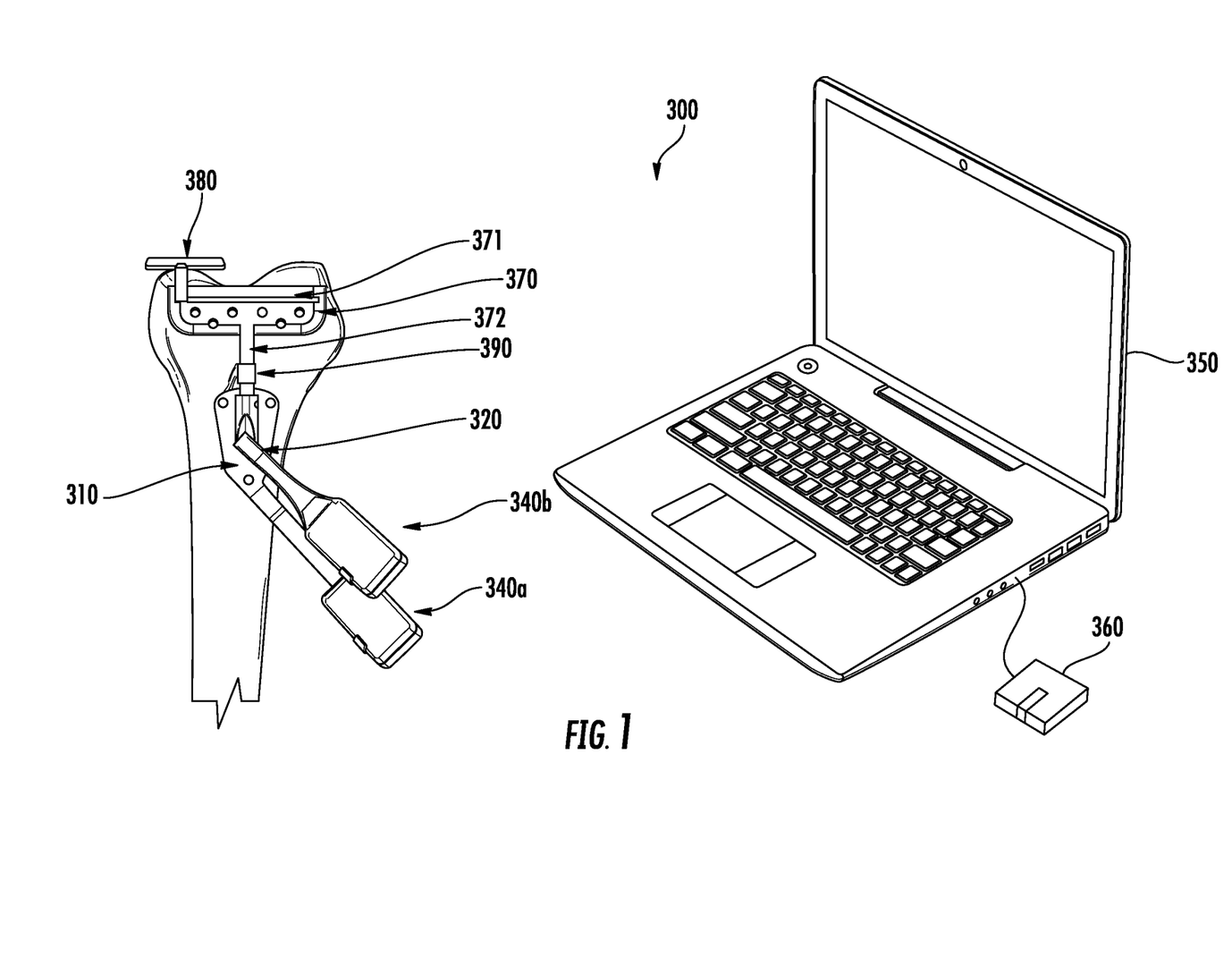
FIG. 1 provides a diagrammatic view of an example sensor system used to measure orientation and position of a cutting guide relative to the patient's anatomy consistent with certain disclosed embodiments.

FIG. 1 provides a view depicting an example knee surgical system to measure orientation and position of a cutting guide relative to the patient's anatomy. As illustrated in FIG. 1, the knee surgical system provides a solution for registering an anatomic axis or plane, measuring the orientation of the cutting guide relative to the anatomy and displaying this information in real-time. The system also provides a solution for tracking the position of the cutting guide relative to an anatomic surface. Those skilled in the art will recognize that embodiments consistent with the presently disclosed systems and methods may be employed in any environment involving arthroplastic procedures, such as the hip and shoulder.

Figure 4:
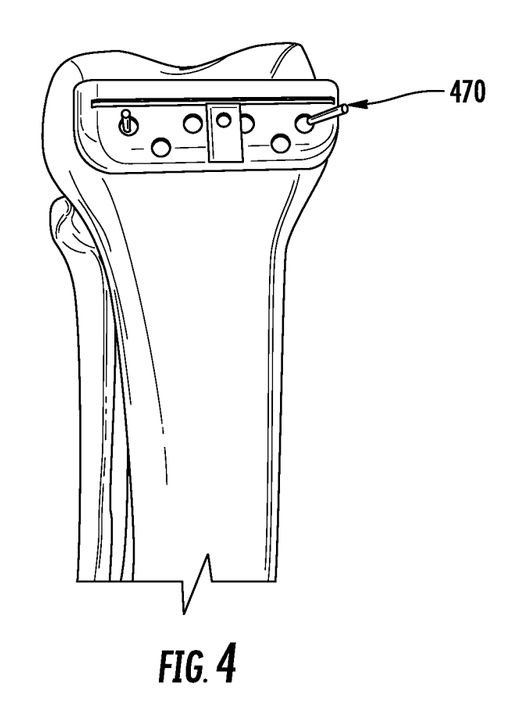
FIG. 4 provides a view of an example cutting guide attached to a bone after desired orientation and position has been achieved.

As illustrated in FIG. 1, the system 300 comprises sensing modules 340 coupled to a processing and display unit 350. One of modules 340a is rigidly attached to the bone via base 310. The other module 340b is attached to base 310 via a mechanism 320 (e.g. ball and socket) that allows for relative rotation between the two modules around at least one axis. Module 340b is also attached to a cutting guide 370 via a sliding mechanism that only allows for relative motion along the long axis of the connecting shaft 372. Cutting guide 370 comprises a cutting slot 371 to guide the cutting instrument such as the blade of an oscillating saw. The cutting guide 370 may also include a magnetic field generator 390, which could be a permanent magnet, rigidly attached to it. The cutting guide also has holes to allow attachment of the guide to the bone via pins or screws once the desired orientation and position of the guide has been achieved. Once the cutting guide is attached to the bone, the positioning mechanism is detached from the guide and removed from the bone. This allows unimpeded cutting of the bone using an oscillating saw. Referring now to FIG. 4, an example cutting guide 470 attached to the bone after desired orientation and position is achieved using the techniques described herein is shown. As shown in FIG. 4, the sensing module(s) can be removed after desired orientation and position is achieved. The cutting guide is also removably coupled to depth gauge 380 of known dimensions. One end of the depth gauge 380 is designed to mate with slot 371 and the other end is designed to mate with one or more anatomic surfaces and/or landmarks such as a femoral condyle as shown in FIG. 1.

The modules 340 may also include one or more inertial measurement units (IMUs). According to one embodiment, IMUs may include or embody one or more of gyroscopes and accelerometers, which are also fixed to each bone. The IMU's may also include magnetometers or magnetic sensors. The IMU may measure rotational motion and/or orientation in a reference coordinate frame or relative to a starting position or another IMU. They may also measure the strength and/or direction of a magnetic field, for example the strength and direction of the magnetic field emanating from magnetic field generator 390. The modules 340 may be attached to the bone using pins or screws commonly used in orthopedic surgery. Inertial measurement units consistent with the disclosed embodiments are described in greater detail below with respect to the schematic diagram of FIG. 3.

The modules 340 associated with the presently disclosed system may each be configured to communicate wirelessly with each other and to a processing and display unit 350 that can be a laptop computer, PDA, or any portable or desktop computing device. The wireless communication can be achieved via any standard radio frequency communication protocol such Bluetooth, Wi Fi, ZigBee, etc., or a custom protocol. In some embodiments, wireless communication is achieved via wireless communication transceiver 360, which may be operatively connected to processing and display unit 350.

The processing and display unit 350 runs software that calculates orientation and position of the cutting guide based on the sensor readings and displays the information on a screen in a variety of ways based on surgeon preferences. The surgeon or surgical assistants can interact with the processing unit either via a keyboard, wired or wireless buttons, touch screens, voice activated commands, or any other technologies that currently exist or may be developed in the future.

In addition to their role as described above, IMU's also allow a means for the system to register axes and/or anatomic planes as described herein. Once registered, modules 340 can be used to measure the orientation of cutting guide 370 relative to one or more axes or planes associated with the patient's bone.

In certain example embodiments, each IMU consists of 3-axis acceleration (accelerometers), 3-axis angular rate (gyroscope) sensors and, a 3-axis magnetometer. The accelerometers and gyroscopes in the IMU work collectively to provide an accurate estimate of angular motion that can be processed to calculate orientation relative in a reference coordinate frame. The magnetometer measures the strength and direction of a magnetic field, such as the field emanating from magnetic field generator 390, which can be utilized to estimate position of the cutting guide 370 relative to an anatomic surface.

Figure 2A:
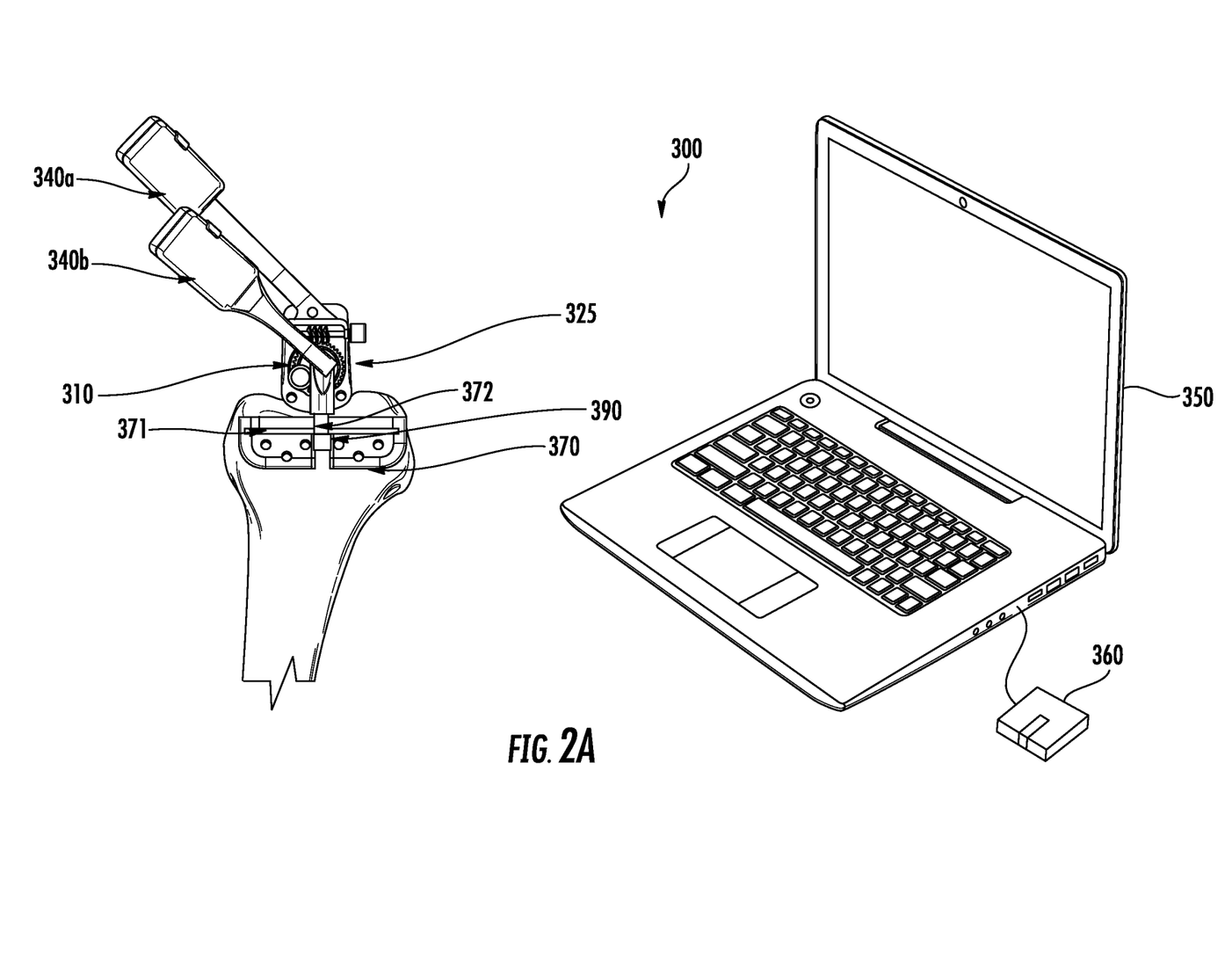
FIG. 2A provides a diagrammatic view of example components associated with an alternate embodiment of a sensor system used to measure orientation and position of a cutting guide relative to the patient's anatomy such as that illustrated in FIG. 1.

An alternate embodiment, illustrated in FIG. 2A, utilizes a mechanical geared connection 325 between base 310 and module 340b which allows the user to change the relative orientation between base 310 and module 340b by turning a knob. In contrast to the freehand motion of the first embodiment, this allows for more precise control of relative motion between the two modules and thereby more precise control of the orientation of cutting guide 370.

Figure 2B:
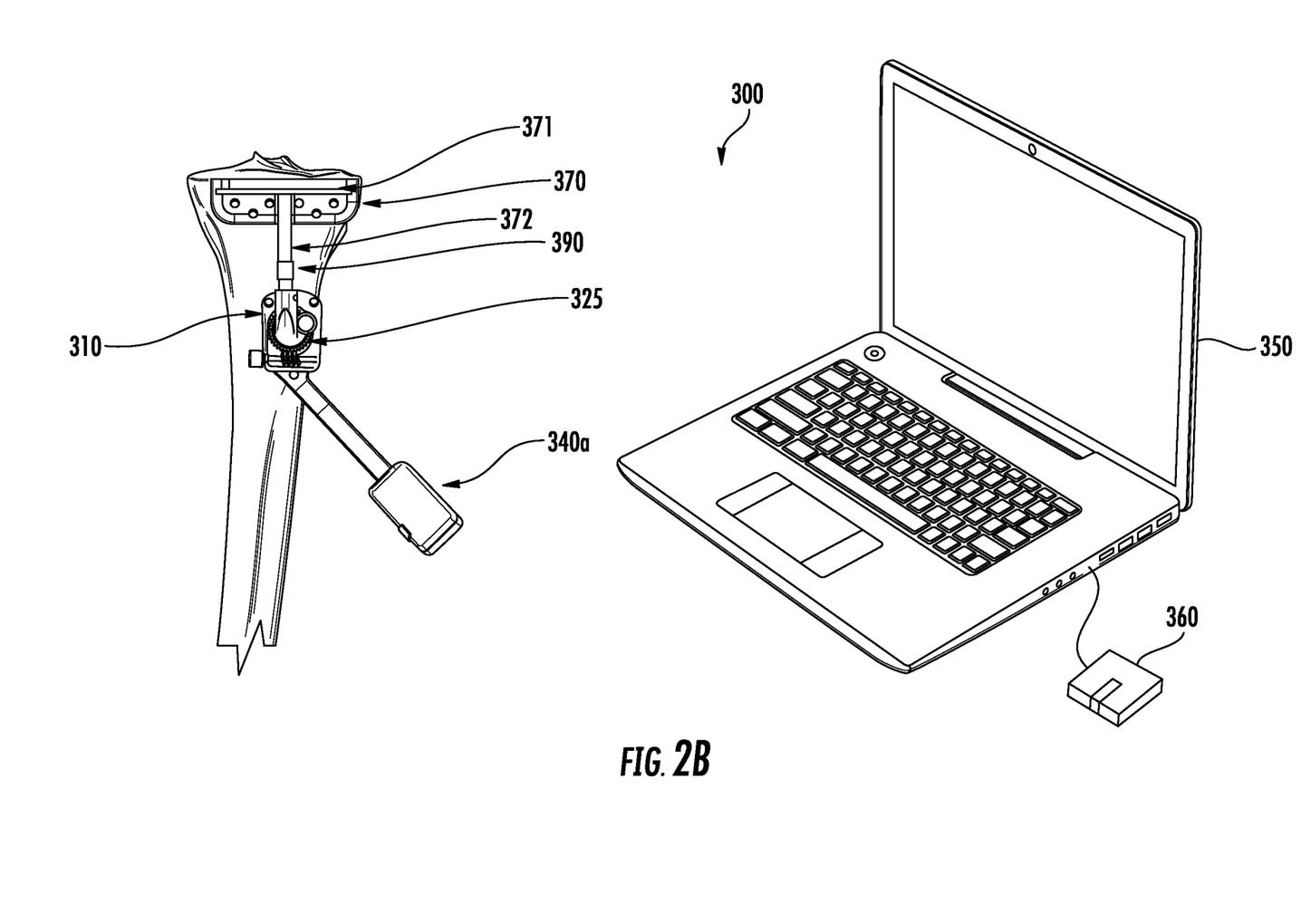
FIG. 2B provides a diagrammatic view of example components associated with an alternate embodiment of a sensor system used to measure orientation and position of a cutting guide relative to the patient's anatomy such as that illustrated in FIG. 1.

In yet another alternate embodiment, illustrated in FIG. 2B, only one module 340a is utilized. In this case, a miniature rotary encoder is integrated with the mechanical geared connection 325. The rotary encoder is coupled with module 340a and measures changes in orientation of cutting guide 370. This information is then transmitted via controller 341c to processor 351. This configuration eliminates the need for a separate module 340b to track changes in the relative orientation of cutting guide 370 and reduces cost and complexity of the system.

In yet another embodiment, the mechanical geared connection 325 includes miniature robotic actuators such stepper motors, servo motors, or other such electrical motors to automatically move the cutting guide 370 to a desired positon and orientation as specified by the surgeon. For example, the processing and display unit 350 can be communicatively coupled to the cutting guide 370 such that the processing and display unit 350 can transmit control signals that cause the robotic actuators in the mechanical geared connection 325 to actuate and move the cutting guide 370 a target position with respect to the patient's anatomy.

Figure 3:
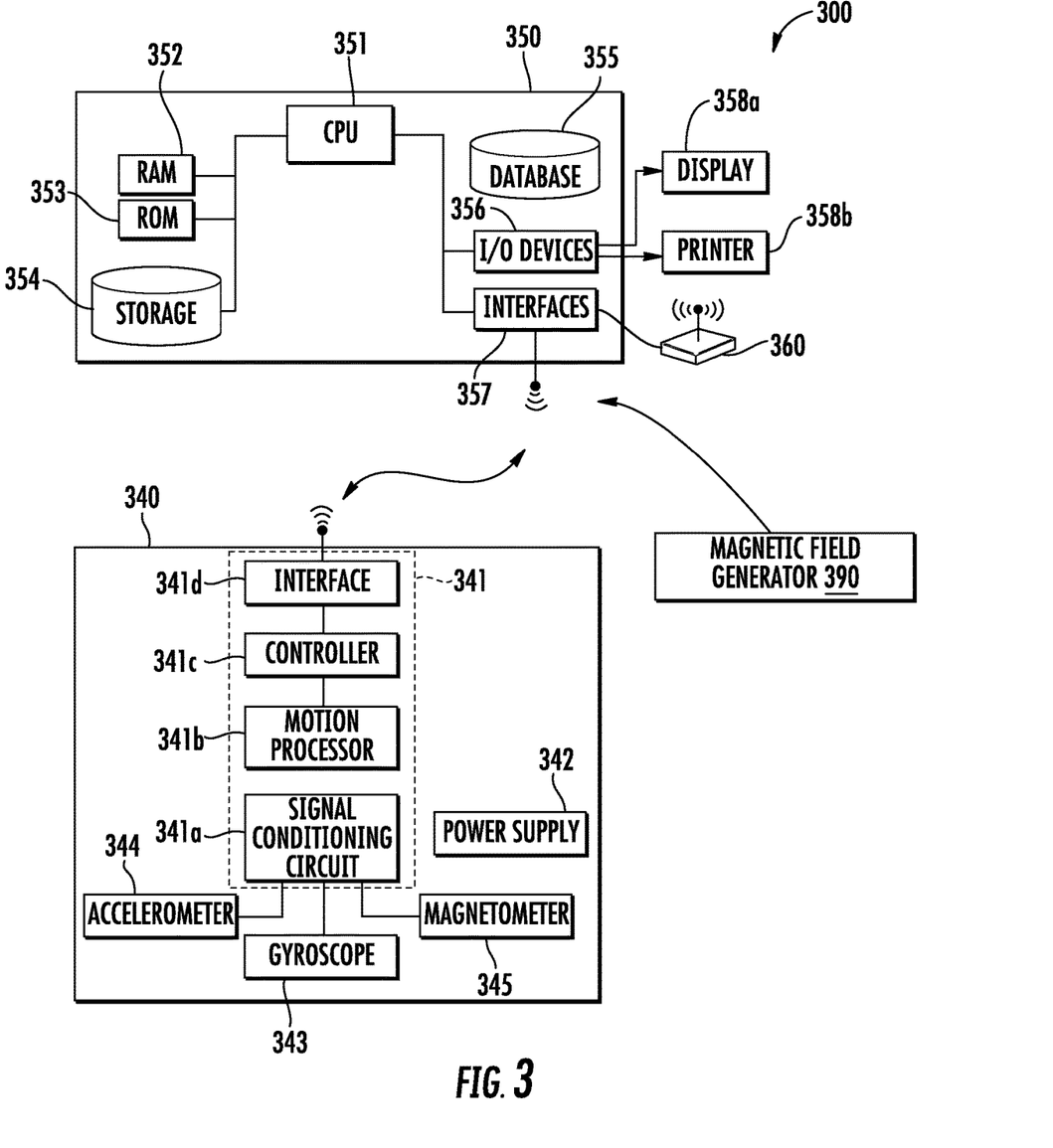
FIG. 3 provides a schematic view of example components associated with a sensor system used to measure orientation and position of a cutting guide relative to the patient's anatomy, such as that illustrated in FIGS. 1, 2A, and 2B.

FIG. 3 provides a schematic diagram illustrating certain exemplary subsystems associated with system 300 and its constituent components. Specifically, FIG. 3 is a schematic block diagram depicting exemplary subcomponents of processing and display unit 350, and sensing modules 340. Those skilled in the art will recognize that embodiments consistent with the presently disclosed systems and methods may be employed in any environment involving arthroplastic procedures, such as the hip, knee and shoulder.

For example, in accordance with the exemplary embodiment illustrated in FIG. 3, system 300 may embody a system for intra-operatively—and in real-time or near real-time—measuring orientation and position of a cutting guide used in knee surgery. As illustrated in FIG. 3, system 300 may include a processing device (such as processing and display unit 350 (or other computer device for processing data received by system 300)), and one or more wireless communication transceivers 360 for communicating with the sensors attached to the patient's anatomy (not shown). The components of system 300 described above are examples only, and are not intended to be limiting. Indeed, it is contemplated that additional and/or different components may be included as part of system 300 without departing from the scope of the present disclosure. For example, although wireless communication transceiver 360 is illustrated as being a standalone device, it may be integrated within one or more other components, such as processing and display unit 350. Thus, the configuration and arrangement of components of system 300 illustrated in FIG. 3 are intended to be examples only.

Processing and display unit 350 may include or embody any suitable microprocessor-based device configured to process and/or analyze information indicative of orientation and position of cutting guide 370 relative to the patient's bone. According to one embodiment, processing and display unit 350 may be a general purpose computer programmed with software for receiving, processing, and displaying information indicative of the orientation and position of the cutting guide. According to other embodiments, processing and display unit 350 may be a special-purpose computer, specifically designed to communicate with, and process information for, other components associated with system 300. Individual components of, and processes/methods performed by, processing and display unit 350 will be discussed in more detail below.

Processing and display unit 350 may be communicatively coupled to the sensor module(s) (and any additional orientation sensors (not shown) used in system 300) and may be configured to receive, process, and/or analyze data measured by the modules 340. According to one embodiment, processing and display unit 350 may be wirelessly coupled to modules 340 via wireless communication transceiver(s) 360 operating any suitable protocol for supporting wireless (e.g., wireless USB, ZigBee, Bluetooth, Wi-Fi, etc.) In accordance with another embodiment, processing system 350 may be wirelessly coupled to modules 340, which, in turn, may be configured to collect data from the other constituent sensors and deliver it to processing and display unit 350. In accordance with yet another embodiment, certain components of processing and display unit 350 (e.g. I/O devices 356) may be suitably miniaturized for integration with modules 340.

Wireless communication transceiver(s) 360 may include any device suitable for supporting wireless communication between one or more components of system 300. As explained above, wireless communication transceiver(s) 360 may be configured for operation according to any number of suitable protocols for supporting wireless, such as, for example, wireless USB, ZigBee, Bluetooth, Wi-Fi, or any other suitable wireless communication protocol or standard. According to one embodiment, wireless communication transceiver 360 may embody a standalone communication module, separate from processing and display unit 350. As such, wireless communication transceiver 360 may be electrically coupled to processing and display unit 350 via USB or other data communication link and configured to deliver data received therein to processing and display unit 350 for further processing/analysis. According to other embodiments, wireless communication transceiver 360 may embody an integrated wireless transceiver chipset, such as the Bluetooth, Wi-Fi, NFC, or 802.11x wireless chipset included as part of processing and display unit 350.

As explained, processing and display unit 350 may be any processor-based computing system that is configured to receive placement parameters associated with an orthopedic instrument, store anatomic registration information, analyze the received placement parameters to extract data indicative of the placement of the surgical instrumentation with respect to the patient's anatomy, and output the extracted data in real-time or near real-time. Non-limiting examples of processing and display unit 350 include a desktop or notebook computer, a tablet device, a smartphone, wearable or handheld computers, or any other suitable processor-based computing system.

For example, as illustrated in FIG. 3, processing and display unit 350 may include one or more hardware and/or software components configured to execute software programs, such as software tracking placement parameters associated with a prosthetic component of orthopedic joint and displaying information indicative of the placement of the component. According to one embodiment, processing and display unit 350 may include one or more hardware components such as, for example, a central processing unit (CPU) or microprocessor 351, a random access memory (RAM) module 352, a read-only memory (ROM) module 353, a memory or data storage module 354, a database 355, one or more input/output (I/O) devices 356, and an interface 357. Alternatively and/or additionally, processing and display unit 350 may include one or more software media components such as, for example, a computer-readable medium including computer-executable instructions for performing methods consistent with certain disclosed embodiments. It is contemplated that one or more of the hardware components listed above may be implemented using software. For example, storage 354 may include a software partition associated with one or more other hardware components of processing and display unit 350. Processing and display unit 350 may include additional, fewer, and/or different components than those listed above. It is understood that the components listed above are examples only and not intended to be limiting.

CPU 351 may include one or more processors, each configured to execute instructions and process data to perform one or more functions associated with processing and display unit 350. As illustrated in FIG. 3, CPU 351 may be communicatively coupled to RAM 352, ROM 353, storage 354, database 355, I/O devices 356, and interface 357. CPU 351 may be configured to execute sequences of computer program instructions to perform various processes, which will be described in detail below. The computer program instructions may be loaded into RAM 352 for execution by CPU 351.

RAM 352 and ROM 353 may each include one or more devices for storing information associated with an operation of processing and display unit 350 and/or CPU 351. For example, ROM 353 may include a memory device configured to access and store information associated with processing and display unit 350, including information for identifying, initializing, and monitoring the operation of one or more components and subsystems of processing and display unit 350. RAM 352 may include a memory device for storing data associated with one or more operations of CPU 351. For example, ROM 353 may load instructions into RAM 352 for execution by CPU 351.

Storage 354 may include any type of mass storage device configured to store information that CPU 351 may need to perform processes consistent with the disclosed embodiments. For example, storage 354 may include one or more magnetic and/or optical disk devices, such as hard drives, CD-ROMs, DVD-ROMs, or any other type of mass media device. Alternatively or additionally, storage 354 may include flash memory mass media storage or other semiconductor-based storage medium.

Database 355 may include one or more software and/or hardware components that cooperate to store, organize, sort, filter, and/or arrange data used by processing and display unit 350 and/or CPU 351. For example, database 355 may include historical data such as, for example, stored placement data associated with the orthopedic joint. CPU 351 may access the information stored in database 355 to provide a comparison between previous joint component placement and current (i.e., real-time) placement data. CPU 351 may also analyze current and previous placement parameters to identify trends in historical data. These trends may then be recorded and analyzed to allow the surgeon or other medical professional to compare the placement parameters with different prosthesis designs and patient demographics. It is contemplated that database 355 may store additional and/or different information than that listed above.

I/O devices 356 may include one or more components configured to communicate information with a user associated with system 300. For example, I/O devices may include a console with an integrated keyboard and mouse to allow a user to input parameters associated with processing and display unit 350. I/O devices 356 may also include a display including a graphical user interface (GUI) for outputting information on a display monitor 358a. In certain embodiments, the I/O devices may be suitably miniaturized and integrated with tool 310. I/O devices 356 may also include peripheral devices such as, for example, a printer 358b for printing information associated with processing and display unit 350, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 357 may include one or more components configured to transmit and receive data via a communication network, such as the Internet, a local area network, a workstation peer-to-peer network, a direct link network, a wireless network, or any other suitable communication platform. For example, interface 357 may include one or more modulators, demodulators, multiplexers, demultiplexers, network communication devices, wireless devices, antennas, modems, and any other type of device configured to enable data communication via a communication network. According to one embodiment, interface 357 may be coupled to or include wireless communication devices, such as a module or modules configured to transmit information wirelessly using Wi-Fi or Bluetooth wireless protocols. Alternatively or additionally, interface 357 may be configured for coupling to one or more peripheral communication devices, such as wireless communication transceiver 360.

As explained, system consists of modules 340 comprising at least one magnetometer 345 that measure the direction and intensity of a magnetic field. These magnetometers are used to measure the direction and intensity of the magnetic field emanating from a magnetic field generator 390 (e.g., the magnetic field generator illustrated in FIGS. 1, 2A, and 2B).

For example the magnetic field generator 390 could be a permanent magnet or electromagnet (i.e. a wound coil through which current is passed). In the case of an electromagnet, one or more coils may be utilized to create multiple magnetic fields that are at known orientations to each other.

Module 340 may also include one or more subcomponents configured to detect and transmit information that either represents the 3-dimensional orientation or can be used to derive the orientation of the module 340 (and, by extension, any object that is affixed relative to modules 340, such as a patient's bone). Module 340 may embody a device capable of determining a 3-dimensional orientation associated with any body to which module 340 is attached. According to one embodiment, orientation sensor(s) in module 340 may be an inertial measurement unit including a microprocessor 341, a power supply 342, and one or more of a gyroscope 343, an accelerometer 344, or a magnetometer 345.

According to one embodiment, the inertial measurement units in 340 may contain a 3-axis gyroscope 343, a 3-axis accelerometer 344, and a 3-axes magnetometer 345. It is contemplated, however, that fewer of these devices with fewer axes can be used without departing from the scope of the present disclosure. For example, according to one embodiment, inertial measurement units may include only a gyroscope and an accelerometer, the gyroscope for calculating the orientation based on the rate of rotation of the device, and the accelerometer for measuring earth's gravity and linear motion, the accelerometer providing corrections to the rate of rotation information (based on errors introduced into the gyroscope because of device movements that are not rotational or errors due to biases and drifts). In other words, the accelerometer may be used to correct the orientation information collected by the gyroscope. Similarly the magnetometer 345 can be utilized to measure a magnetic field and can be utilized to further correct gyroscope errors. Thus, while all three of gyroscope 343, accelerometer 344, and magnetometer 345 may be used, orientation measurements may be obtained using as few as one of these devices. The use of additional devices increases the resolution and accuracy of the orientation information and, therefore, may be advantageous when orientation accuracy is important. The information for the different sensors may be "fused" using appropriate sensor fusion algorithms and filtering techniques. An example of filtering technique that could be used with this invention is a Kalman Filter.

As illustrated in FIG. 3, microprocessor 341 of modules 340 may include different processing modules or cores, which may cooperate to perform various processing functions. For example, microprocessor 341 may include, among other things, an interface 341d, a controller 341c, a motion processor 341b, and signal conditioning circuitry 341a. Controller 341c may also be configured to control and receive conditioned and processed data from one or more of gyroscope 343, accelerometer 344, and magnetometer 345 and transmit the received data to one or more remote receivers. The data may be pre-conditioned via signal conditioning circuitry 341a, which includes amplifiers and analog-to-digital converters or any such circuits. The signals may be further processed by a motion processor 341b. Motion processor 341b may be programmed with so-called "motion fusion" algorithms to collect and process data from different sensors to generate error corrected orientation and position information. The orientation information may be a mathematically represented as an orientation or rotation quaternion, euler angles, direction cosine matrix, rotation matrix of any such mathematical construct for representing orientation known in the art. Accordingly, controller 341c may be communicatively coupled (e.g., wirelessly via interface 341d as shown in FIG. 3, or using a wireline protocol) to, for example, processing and display unit 350 and may be configured to transmit the data received from one or more of gyroscope 343, accelerometer 344, and magnetometer 345 to processing and display unit 350, for further analysis.

Interface 341d may include one or more components configured to transmit and receive data via a communication network, such as the Internet, a local area network, a workstation peer-to-peer network, a direct link network, a wireless network, or any other suitable communication platform. For example, interface 341d may include one or more modulators, demodulators, multiplexers, demultiplexers, network communication devices, wireless devices, antennas, modems, and any other type of device configured to enable data communication via a communication network. According to one embodiment, interface 341d may be coupled to or include wireless communication devices, such as a module or modules configured to transmit information wirelessly using Wi-Fi or Bluetooth wireless protocols. As illustrated in FIG. 3, modules 340 may be powered by power supply 342, such as a battery, fuel cell, MEMs microgenerator, or any other suitable compact power supply.

Importantly, although microprocessor 341 of module 340 is illustrated as containing a number of discrete modules, it is contemplated that such a configuration should not be construed as limiting. Indeed, microprocessor 341 may include additional, fewer, and/or different modules than those described above with respect to FIG. 3, without departing from the scope of the present disclosure. Furthermore, in other instances of the present disclosure that describe a microprocessor are contemplated as being capable of performing many of the same functions as microprocessor 341 of modules 340 (e.g., signal conditioning, wireless communications, etc.) even though such processes are not explicitly described with respect to microprocessor 341. Those skilled in the art will recognize that many microprocessors include additional functionality (e.g., digital signal processing functions, data encryption functions, etc.) that are not explicitly described here. Such lack of explicit disclosure should not be construed as limiting. To the contrary, it will be readily apparent to those skilled in the art that such functionality is inherent to processing functions of many modern microprocessors, including the ones described herein.

Microprocessor 341 may be configured to receive data from one or more of gyroscope 343, accelerometer 344, and magnetometer 345, and transmit the received data to one or more remote receivers. Accordingly, microprocessor 341 may be communicatively coupled (e.g., wirelessly (as shown in FIG. 3, or using a wireline protocol) to, for example, processing and display unit 350 and configured to transmit the orientation and position data received from one or more of gyroscope 343, accelerometer 344, and magnetometer 345 to processing and display unit 350, for further analysis. As illustrated in FIG. 3, microprocessor 341 may be powered by power supply 342, such as a battery, fuel cell, MEMs micro-generator, or any other suitable compact power supply.

Anatomic Registration

As explained, in order for system 300 to accurately estimate orientation of the surgical cutting guide, it must register one or more anatomic axes or planes of interest. This allows the system to convert the orientation as derived from the information from the sensors into the appropriate anatomical components such as the varus-valgus and flexion-extension components. For example, modules 340 may have their own X, Y, Z coordinate system and the process of registration establishes the relationship between the modules' coordinate system and the patient's anatomy. The information that can then be displayed on a virtual bone model in the display unit 350. The term "anatomic axis or plane," is used herein to refer to a plane, vector, or coordinate system related or relevant to a particular object, such as a bone or other portion of the patient's anatomy. This disclosure contemplates using any appropriate registration technique known in the art to register the patient's anatomy.

One exemplary process for registering modules 340 to the patient's femur is by moving the femur and attached modules 340 through a specific range of motion such as flexion-extension, abduction-adduction, and/or rotation. Sensor data is collected throughout these motions either continuously or at discrete points. From this data, the mechanical axis of the femur can be derived.

An alternate process for registering modules 340 to the patient's anatomy is by aligning the module along certain bony landmarks. For example, system 300 may be configured to measure orientation of modules 340 while they are removably attached to an elongate registration tool or spike that is aligned to specific anatomical landmarks either by extramedullary or intramedullary means. Using geometrical relationships associated with the anatomical landmarks, the information indicative of the orientation of modules 340 can be used to derive a coordinate space that is representative of the bone.

It will be apparent to those skilled in the art that various modifications and variations can be made to the disclosed systems and methods for measuring placement parameters associated with surgical instrumentation and tools in orthopedic arthroplastic procedures. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A system for estimating an orientation, the system comprising:
    a base attached to a bone of a patient;
    a surgical instrument mechanically coupled to the base;
    a mechanism configured to adjust a relative position of the surgical instrument with respect to the base;
    a first orientation sensor coupled to the base and configured to detect information indicative of an orientation of the bone;
    a second orientation sensor coupled to the surgical instrument and configured to detect information indicative of an orientation of the surgical instrument; and
    a processor communicatively coupled to the first and second orientation sensors and configured to:
        receive information indicative of an orientation of an anatomic axis or plane of the bone; and
        estimate an angle between the surgical instrument and the anatomic axis or plane.

2. The system of claim 1, wherein at least one of the first and second orientation sensors comprise an inertial measurement unit that includes at least one of a gyroscope, an accelerometer, or a magnetometer.

3. The system of claim 1, wherein the mechanism comprises a ball and socket that allows for relative rotation between the surgical instrument and the base around at least one axis.

4. The system of claim 1, wherein the mechanism comprises a sliding mechanism that allows for relative motion between the surgical instrument and the base along a connecting shaft.

5. The system of claim 1, further comprising a depth gauge, wherein the surgical instrument is coupled to the depth gauge.

6. The system of claim 1, wherein the mechanism comprises a geared connection.

7. A system for estimating a position, the system comprising:
    a base attached to a bone of a patient;
    a surgical instrument mechanically coupled to the base;
    a mechanism configured to adjust a relative position of the surgical instrument with respect to the base;
    a magnetic field generator attached to one of the surgical instrument or the base;
    one or more magnetic sensors coupled to the other of the base or the surgical instrument and configured to detect information indicative of a position of the surgical instrument; and
    a processor communicatively coupled to the magnetic sensors and configured to:
    receive information indicative of a first position of the surgical instrument relative to an anatomic surface of the bone; and
    estimate change in position of the surgical instrument relative to the anatomic surface of the bone.

8. The system of claim 7, wherein the magnetic field generator is a permanent magnet.

9. The system of claim 7, wherein the magnetic field generator is a solenoid.

10. The system of claim 7, wherein each of the one or more magnetic sensors comprises one or more magnetometers.

11. The system of claim 7, wherein the mechanism comprises a ball and socket that allows for relative rotation between the surgical instrument and the base around at least one axis.

12. The system of claim 7, wherein the mechanism comprises a sliding mechanism that allows for relative motion between the surgical instrument and the base along a connecting shaft.

13. The system of claim 7, further comprising a depth gauge, wherein the surgical instrument is coupled to the depth gauge.

14. The system of claim 7, wherein the mechanism comprises a geared connection.

15. A system for automated positioning, the system comprising:
    a base attached to a bone of a patient;
    a surgical instrument mechanically coupled to the base;
    a mechanism configured to adjust a relative position of the surgical instrument with respect to the base;

a orientation sensor coupled to the base and configured to detect information indicative of an orientation of the bone; and a processor communicatively coupled to the orientation sensor and the surgical instrument and configured to:

receive information indicative of an orientation of an anatomic axis or plane of the bone; and control the surgical instrument to a target position with respect to the anatomic axis or plane of the bone.

16. The system of claim 15, wherein the surgical instrument comprises one or more robotic actuators coupled to the mechanism, wherein the one or more robotic actuators are configured to move the surgical instrument with respect to the base.

17. The system of claim 15, wherein the mechanism comprises a geared connection having a rotary encoder.

18. The system of claim 16, wherein the one or more robotic actuators are stepper motors.

19. The system of claim 16, wherein the one or more robotic actuators are servo motors.

* * * * *